(12) United States Patent
Hirabayashi et al.

(10) Patent No.: US 7,231,241 B2
(45) Date of Patent: Jun. 12, 2007

(54) PROBE FOR OPTICAL MEASUREMENT INSTRUMENT FOR LIVING BODY AND OPTICAL MEASUREMENT INSTRUMENT FOR LIVING BODY USING THE SAME

(75) Inventors: Yukiko Hirabayashi, Kokubunji (JP); Kenko Uchida, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 153 days.

(21) Appl. No.: 11/070,816

(22) Filed: Mar. 3, 2005

(65) Prior Publication Data

US 2006/0122477 A1    Jun. 8, 2006

(30) Foreign Application Priority Data

Dec. 3, 2004    (JP) .............................. 2004-350778

(51) Int. Cl.
*A61B 5/00*    (2006.01)
(52) U.S. Cl. ...................................... 600/344; 600/340
(58) Field of Classification Search ................ 600/310, 600/322, 323, 340, 344, 473, 476
See application file for complete search history.

(56) References Cited

U.S. PATENT DOCUMENTS

| | | | |
|---|---|---|---|
| 5,803,909 | A | 9/1998 | Maki |
| 2003/0073910 | A1 | 4/2003 | Chance |
| 2004/0054271 | A1* | 3/2004 | Maki et al. ............ 600/341 |
| 2004/0077935 | A1 | 4/2004 | Hirabayashi et al. |

FOREIGN PATENT DOCUMENTS

| | | |
|---|---|---|
| EP | 1 245 192 | 10/2002 |
| EP | 1 407 711 | 4/2004 |
| JP | 2001-286449 | 10/2001 |
| JP | 2002-011012 | 1/2002 |
| JP | 2002-143169 | 5/2002 |
| JP | 2004-313741 | 11/2004 |

OTHER PUBLICATIONS

Medical Physics, vol. 22, No. 12, pp. 1997-2005 (1995).
Proceedings of SPIE, vol. 3597, pp. 230-237.

* cited by examiner

*Primary Examiner*—Eric F. Winakur
(74) *Attorney, Agent, or Firm*—Antonelli, Terry, Stout & Kraus, LLP.

(57) ABSTRACT

Disclosed is a probe for biomeasurement by use of light capable of adjusting positions of incident points and detection points without changing the distance between the incident point and the detection point in accordance with the size of a subject's head, and an optical bioinstrumentation for living body using the probe. The distances between the incident points and the detection points are approximately the same. A gap is formed by removing part of connecting members, rotatable about the incident point and the detection point, around the subject head top portion. The size of the probe is changed by changing the distance between the incident points or the detection points around the gap.

15 Claims, 12 Drawing Sheets

PROBE FOR OPTICAL MEASUREMENT INSTRUMENT FOR LIVING BODY AND OPTICAL MEASUREMENT INSTRUMENT FOR LIVING BODY USING THE SAME

CLAIM OF PRIORITY

The present invention claims priority from Japanese application JP 2004-350778 filed on Dec. 3, 2004, the content of which is hereby incorporated by reference on to this application.

BACKGROUND OF THE INVENTION

The present invention relates to a technique of biomeasurement using light for measurement of the density or density change of metabolites. The present invention particularly relates to a probe for biomeasurement by use of light for the density of metabolites in a subject's head and an optical bioinstrumentation for living body using the same.

"Medical Physics, vol. 22, No. 12, pp. 1997–2005 (1995)" and "Proceedings of SPIE, vol. 3597, pp. 230–237" have already proposed techniques for measuring a blood amount change in a cerebral cortex in accordance with brain activity at multiple points, and displaying the blood amount change as a moving image or still image (optical bioinstrumentation). These techniques employ a rectangular probe having incident optical fibers and detection optical fibers alternately arranged in square lattice configuration.

Since the above square lattice probe cannot be attached tightly to an approximately globular head without difficulty, the following proposals have been already made.

(1) Japanese Published Unexamined Patent Application No. 2001-286449 discloses a optical bioinstrumentation for living body having a branch-like part extended from a linking axis so as to fit to the shape of head.
(2) Japanese Published Unexamined Patent Application No. 2002-143169 discloses an optical bioinstrumentation for living body in which connecting portions of a lattice probe are rotatable and a holder to hold the respective probes is stretchy.
(3) Japanese Published Unexamined Patent Application No. 2002-11012 discloses a probe having square lattice filling plural areas of the head and polygonal members filled among each vertex of the lattice so as to cover the entire head.
(4) Published Japanese Translation of PCT International Publication for Patent Application No. 2002-502653 discloses an apparatus for non-destructively measuring a subject's brain tissue with probes geometrically arranged on the subject's head.
(5) Japanese Published Unexamined Patent Application No. 2004-121702 discloses a probe having 4 sets of diamond arranged incident optical fibers and detection optical fibers to cover the overall globular head, capable of displaying almost all area of a brain surface in one image.

SUMMARY OF THE INVENTION

However, in the above-described optical bioinstrumentations for living body and probes have the following problems.

The diamond arranged probe and lattice probe can be fit to an almost globular head and can display at least an upper half part of the head, i.e., corresponding to the brain surface, in one image. However, if the head size is different, relative measuring areas of brain are shifted, and the measured brain areas are different. That is, if the head size is small, the head-to-parotic areas can be covered, while if the head size is large, the covered area from the head top ends far above the parotic areas. It is said that a language area exists in a brain area around ears. If the head size changes, the language area cannot be covered in some cases.

The present invention has been made to address these problems, and provides a probe for biomeasurement by use of light capable of adjusting positions of incident points and detection points without changing the distance between the incident point and the detection point in accordance with the size of a subject's head, and a optical bioinstrumentation for living body using the probe.

In accordance with the present invention as described above, part of connecting members connecting incident optical fibers and detection optical fibers and part of the optical fibers are removed so as to form a gap (FIG. 1 to be described later) to change the distance between the optical fibers around the gap (FIGS. 3 and 4 to be described later). Even if the head size changes, the optical fibers positioned on the periphery of the probe can be arranged in approximately the same positions on the head, e.g., immediately above an ear (FIGS. 7 to 9 to be described later).

In this manner, the present invention provides a probe which can measure approximately the same position of the subject's head by changing the distance between the optical fibers arranged around the gap or changing the area of the gap.

Hereinbelow, typical aspects of the present invention will be given.

(1) A probe for biomeasurement by use of light comprises: plural emission optical fibers that emit light to a subject with light; plural detection optical fibers that detect light, emitted from the emission optical fibers and propagated inside the subject; plural fixing units that respectively fix the emission optical fibers and the detection optical fibers; and connecting members that respectively connect the plural fixing units, wherein distances between adjacent fixing units connected with the connecting members are approximately the same, and wherein the connecting member is rotatable about the fixing unit, further wherein a gap having a variable area, in which the fixing units and the connecting members are omitted, is provided in a part of the entire area constructed with the plural fixing units and the plural connecting members.
(2) In the probe for biomeasurement by use of light (1), the distance between the fixing units, provided around the gap, and not adjacent to each other, is variable.
(3) The probe for biomeasurement by use of light (1) further comprises a fixing member that fixes the distance between the fixing units, provided around the gap, and not adjacent to each other.
(4) In the probe for biomeasurement by use of light (3), the fixing member has a length adjustment mechanism.
(5) In the probe for biomeasurement by use of light (1), to fix the distance between the fixing units, provided around the gap and not adjacent to each other, the connecting member between the fixing units provided around the gap fixes rotation about the fixing unit.
(6) In the probe for biomeasurement by use of light (1), the fixing unit and the connecting member are removable, so as to increase/decrease the number of the fixing units.
(7) An optical bioinstrumentation for living body comprises: a probe having plural emission optical fibers that emit light to a subject and plural detection optical fibers that detect transmission light, emitted from the emission optical fibers and propagated inside the subject, to be attached to the subject; and a computation unit that calculates the density of metabolites in the subject from the transmission light detected by the probe, wherein the probe has plural fixing units that respectively fix the emission optical fibers and the detection optical fibers and connecting members that respectively connect the plural fixing units, and wherein distances between adjacent fixing units connected with the connecting units are approximately the same, further wherein the connecting member is rotatable about the fixing unit, further wherein a gap having a variable area, in which the fixing units and the connecting members are omitted, is provided in a part of the entire area constructed with the plural fixing units and the plural connecting members.

(8) In the optical bioinstrumentation of (7), the computation unit calculates the density of metabolites in the subject in an approximately middle position between the emission optical fiber and the detection optical fiber as a measuring point, based on a signal detected by the probe.

The aspects of the present invention provide a probe for biomeasurement by use of light capable of adjusting positions of incident points and detection points without changing the distance between the incident point and the detection point in accordance with the size of a subject's head, and a optical bioinstrumentation for living body using the probe.

BRIEF DESCRIPTION OF THE DRAWINGS

The above and other object, features and advantages of the present invention will become more apparent from the following detailed description when taken in conjunction with the accompanying drawings wherein.

DETAILED DESCRIPTION OF THE PREFERRED EMBODIMENT

Hereinbelow, a preferred embodiment of the present invention will now be described in detail in accordance with the accompanying drawings.

Figure 1:
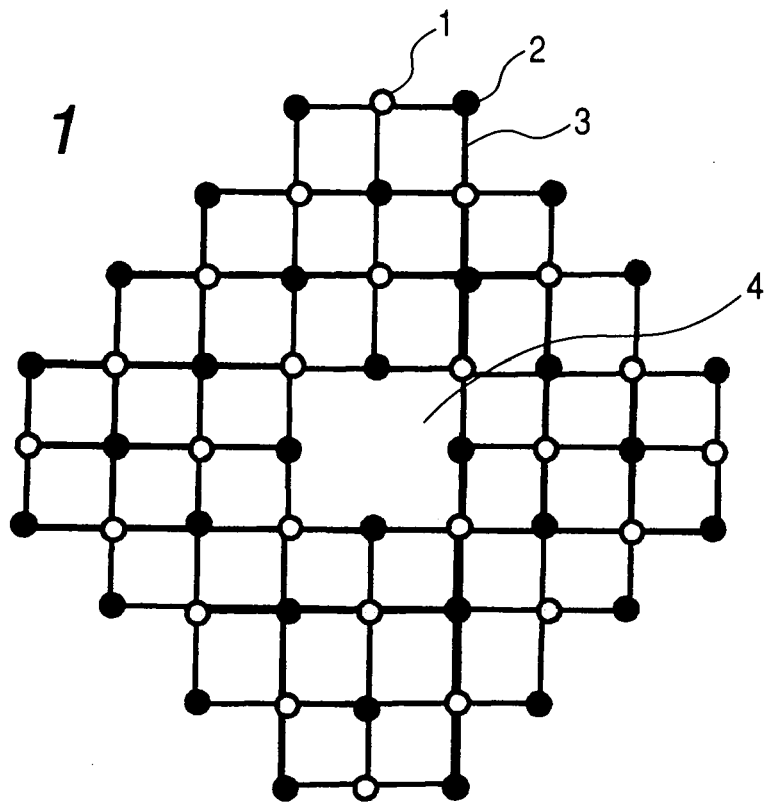
FIG. 1 is an expansion plan view showing the arrangement of a probe for biomeasurement by use of light according to an embodiment of the present invention.

FIG. 1 is an expansion plan view showing the arrangement of a probe for biomeasurement by use of light according to an embodiment of the present invention.

Incident points 1 connected to incident optical fibers and detection points 2 connected to detection optical fibers are connected with connecting members 3, and arranged at approximately the same intervals. The connecting member 3, formed of non-expandable material, maintains an approximately constant distance between the incident point 1 and the detection point 2. The connecting member 3 is rotatable about the positions of the incident point 1 and the detection point 2, such that the probe can be attached along the round shape of a head. The material of the connecting member is, e.g., stiff silicone rubber, resin, gel and the like.

Part of the incident points 1 and the detection points 2, arranged at constant intervals, and the connecting members 3 are removed so as to form a gap 4. This probe is attached to a subject's head such that the gap is positioned on the head top portion. In this manner, in the present invention, a gap 4 without fixing unit and connecting member is provided in a part of the entire area having plural fixing units and plural connecting units. Further, the area of the gap 4 is variable.

Figure 21A:
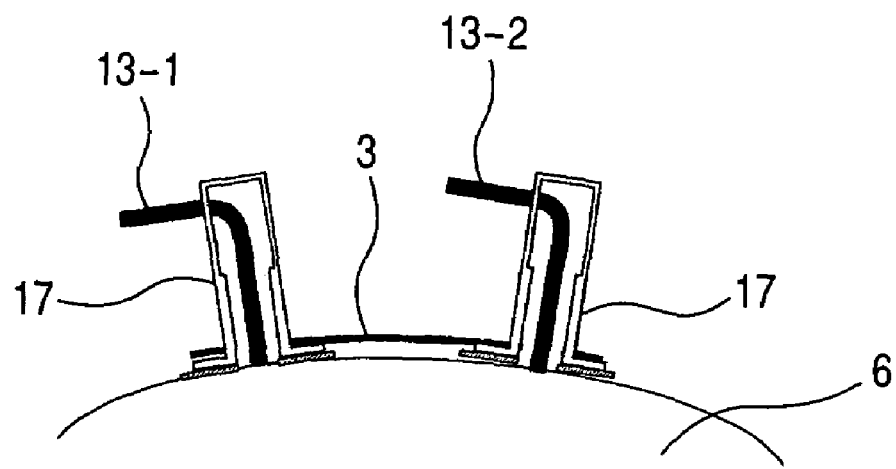
FIG. 21(a) is a partial expanded cross-sectional view showing an example of fixing units to fix the incident optical fiber and the detection optical fiber.

FIG. 21(a) shows an example of the fixing units to fix the incident optical fiber and the detection optical fiber in the probe according to the present invention. An incident optical fiber 13-1 is fixed with a fixing unit 17 such that its end is in contact with the skin of a subject 6. Similarly, a detection optical fiber 13-2 is fixed with the fixing unit 17 such that its end is in contact with the skin of the subject 6. The fixing unit 17 is formed of e.g. Noryl, resin, rubber or the like. Plural fixing units 17 respectively fixing adjacent incident optical fiber 13-1 and detection optical fiber 13-2 are arranged at approximately constant intervals with the connecting members 3.

Figure 21B:
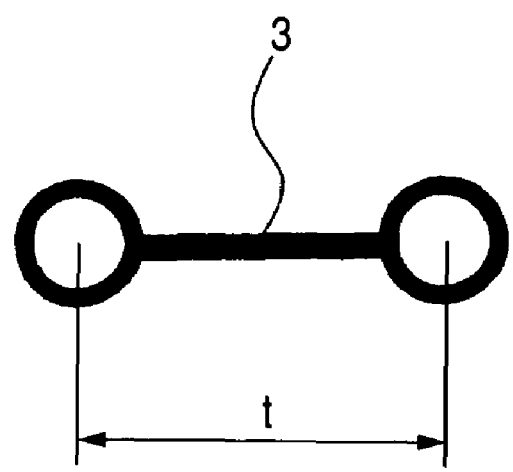
FIG. 21(b) is a schematic explanatory view showing an example of a connecting member.

FIG. 21(b) shows an example of the connecting member in the probe according to the present invention. The connecting member 3 in the present embodiment has two rings connected with each other. The distance between the central points of the two rings is denoted by t. The connecting member 3 fixes the distance between an incident point as a point of contact where the end of the incident optical fiber 13-1 is in contact with the skin of the subject 6 and a detection point as a point of contact where the end of the detection optical fiber 13-2 is in contact with the skin of the subject 6 as the approximately constant distance t. The distance t is set to about 30 mm upon measurement of adult's head. Upon measurement of infant or newborn infant, the distance t is set to 20 mm or 30 mm in accordance with purpose of measurement. The distance t may be changed in accordance with purpose of measurement or difference in subject.

Figure 2:
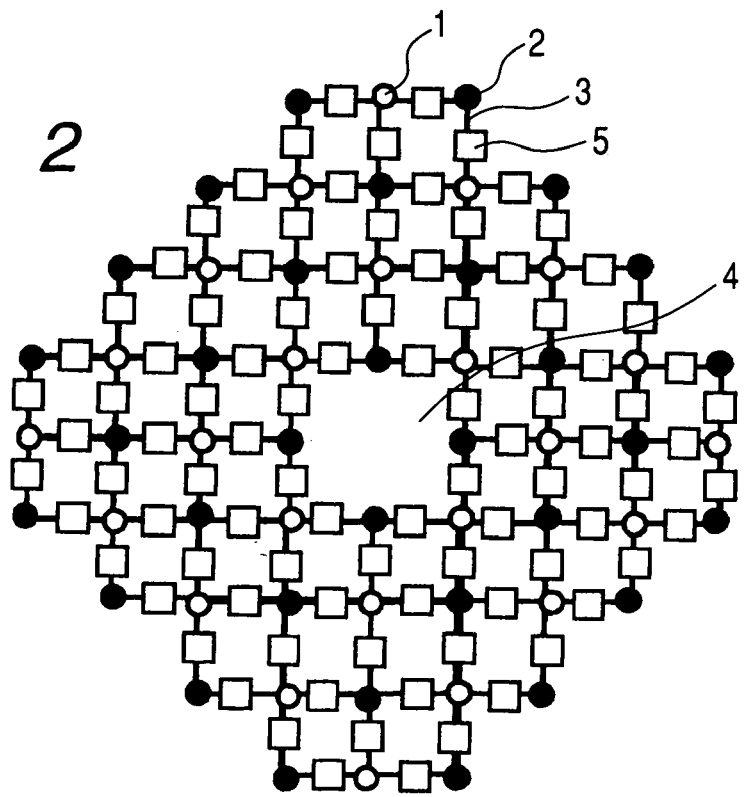
FIG. 2 is an expansion plan view showing the distribution of sampling points in the arrangement in FIG. 1.

FIG. 2 shows the distribution of sampling points (measuring points) 5 in the arrangement in FIG. 1. Measuring light, emitted from a lamp, a light emitting diode, semiconductor laser or the like, is passed through the incident optical fiber from the incident point 1 on the head. The light propagated through a cerebral cortex in the head is sent through the detection optical fiber connected with the detection point 2 to an light emitter such as a photo diode or a photomultiplier tube and is detected. As the intensity of detected light varies in dependent on the status of blood flow in the cerebral cortex, the increase/decrease of blood in the cerebral cortex through which the light has propagated can be measured. The detection signal reflects blood flow information of the entire light-propagated part. However, for the sake of convenience, the approximate central position between the incident point 1 and the detection point 2 is referred to as a sampling point 5, and the measured signal value corresponds to the blood flow information at the sampling point 5. An image of blood flow distribution can be obtained by providing plural sets of incident points and detection points and obtaining blood flow information at the plural sampling points.

Figure 3:
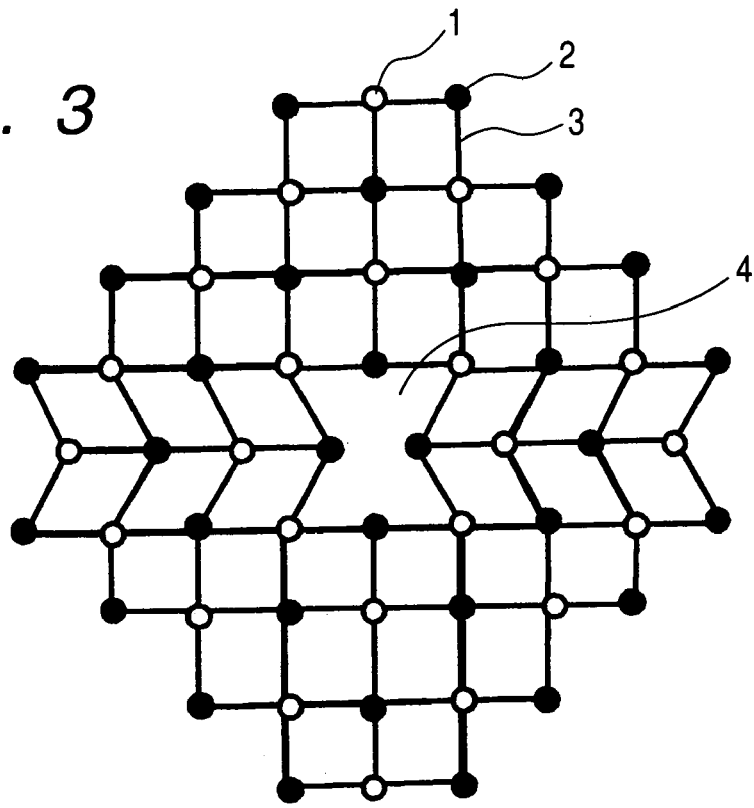
FIG. 3 is an expansion plan view showing a first arrangement of the probe according to the present invention.

FIG. 3 is an expansion plan view showing a first arrangement of the probe according to the present invention. In correspondence with a rather small head, the distance between a pair of opposite detection points is shortened such that the size in one direction is reduced. The direction of size reduction may be a direction from the frontal region to the occipital region, or may be a direction from the left temporal region to the right temporal region, in accordance with a portion of measurement of the head. Further, the positions of incident and detection points may be inversed. In this case, the number of sampling points 5 is the same as that in FIGS. 1 and 2.

Figure 4:
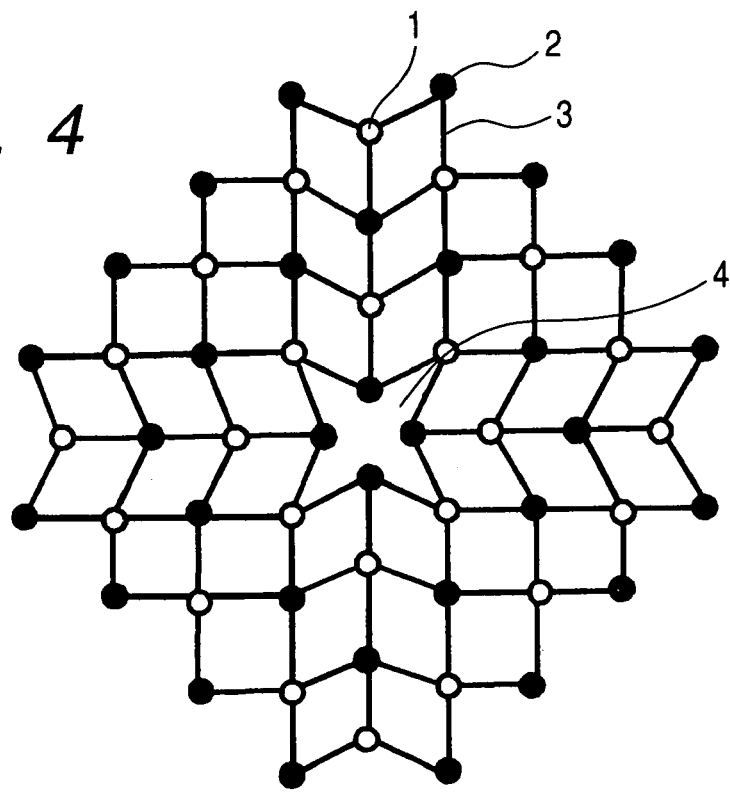
FIG. 4 is an expansion plan view showing a second arrangement of the probe according to the present invention.

FIG. 4 is an expansion plan view showing a second arrangement of the probe according to the present invention. The distances between two pairs of opposite detection points are shortened so as to reduce the size in two directions in accordance with a smaller head. In this case, the size is reduced in the front-back direction and the left-right direction. Also, in this case, the positions of incident and detection points may be inversed. In this case, the number of sampling points 5 is the same as that in FIGS. 1 and 2.

Figure 5:
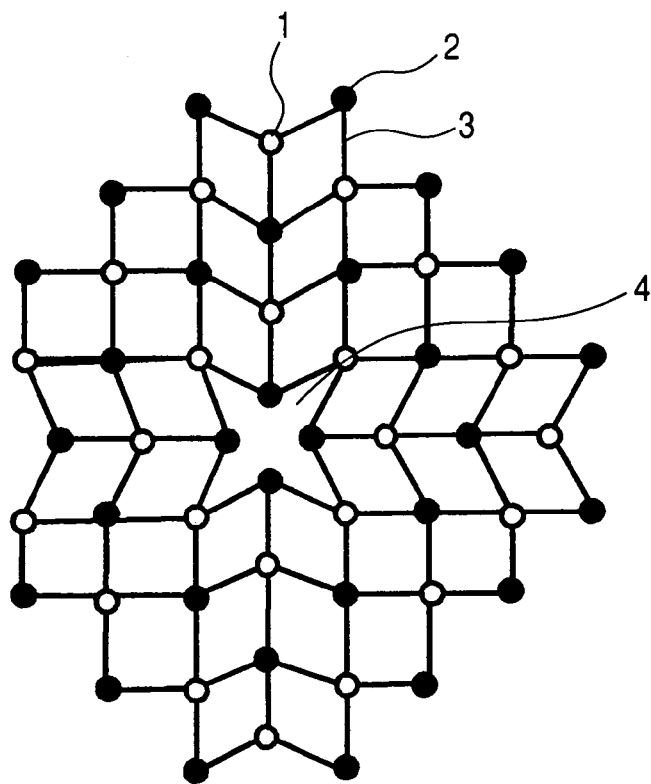
FIG. 5 is an expansion plan view showing a third arrangement of the probe according to the present invention.

FIG. 5 is an expansion plan view showing a third arrangement of the probe according to the present invention. Different from the above arrangements where the same numbers of incident points 1, detection points 2 and sampling points 5 are uniformly provided in the front-back direction and left-right direction, the numbers of these points are changed in accordance with purpose. In this case, the numbers of incident points 1, detection points 2 and sampling points 5 in the frontal region close to the eyes are reduced so as to increase safety. Note that the numbers of incident points 1, detection points 2 and sampling points 5 in temporal regions or occipital region may be reduced in accordance with purpose. Further, a removable mechanism such as a hook may be attached to the probe.

Figure 6:
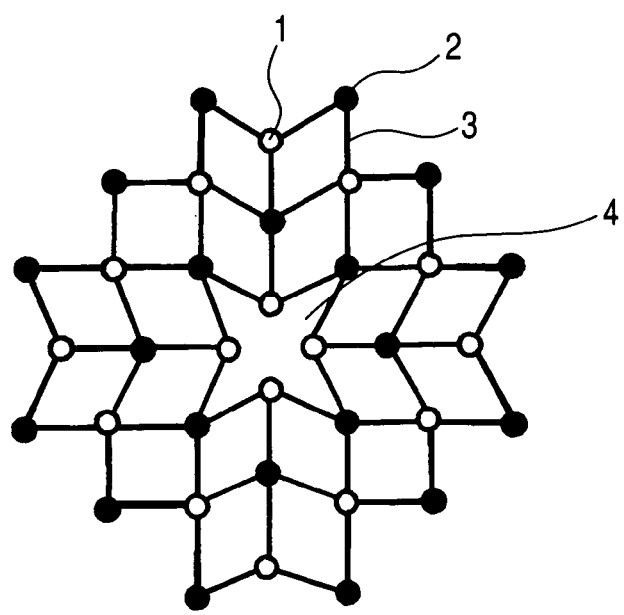
FIG. 6 is an expansion plan view showing a fourth arrangement of the probe according to the present invention.

FIG. 6 is an expansion plan view showing a fourth arrangement of the probe according to the present invention. In this arrangement, the outer peripheral incident and detection points are removed for measurement of further small head of newborn or premature infant. In this case, to increase safety, the positions of the incident points and the detection points are inversed such that the detection points are provided on the outer periphery. Also, in this case, a removable mechanism such as a hook may be attached to the probe if necessary for increase/decrease of incident and detection points.

Figure 7:
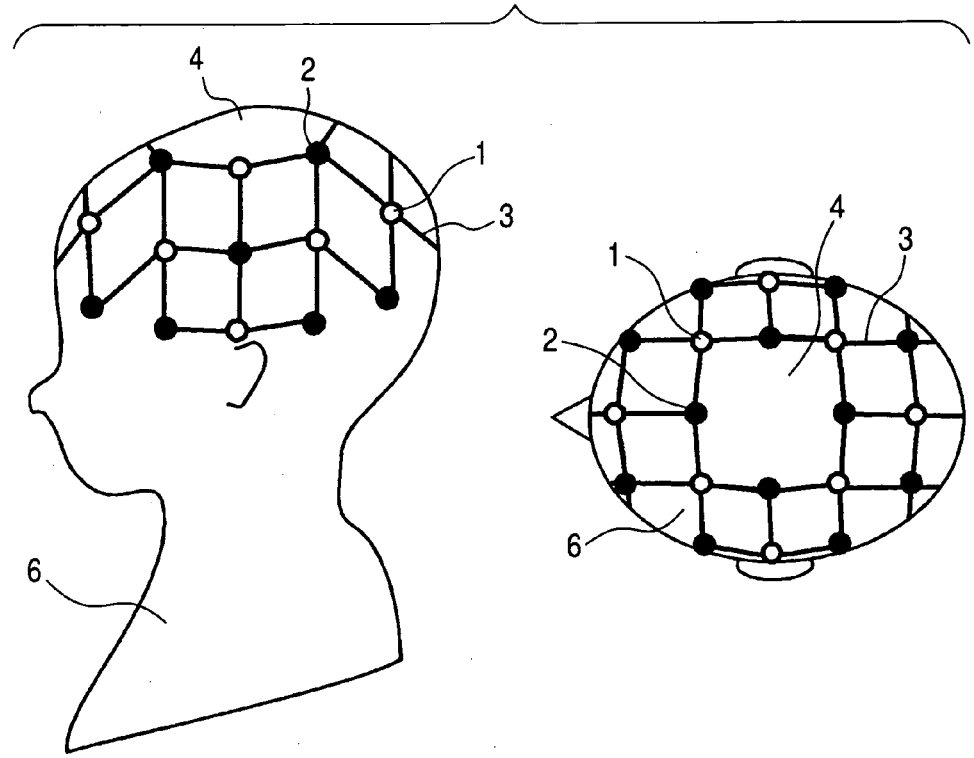
FIG. 7 is side view and top plan view showing an example of the probe in FIG. 6 attached to a subject's head.

FIG. 7 is side view and top plan view showing an example of the probe in FIG. 6 attached to the head of the subject 6. If the head is rather larger than the probe, as the incident point and the detection point on the outer periphery of the gap 4 are away from each other, the gap 4 has an octagonal shape. Further, as the connecting members 3, which are rotatable about the incident and detection points, are fit to the head, the connecting members partially form a diamond mesh structure. The outer periphery of the probe covers portions above the ears.

Figure 8:
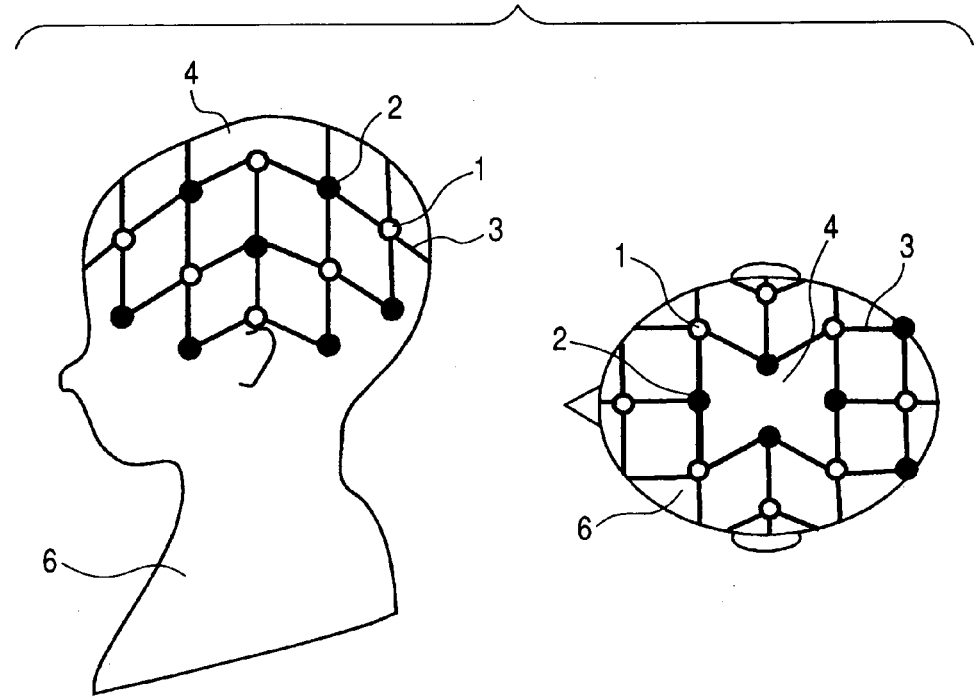
FIG. 8 is side view and top plan view showing another example of the probe in FIG. 6 attached to the subject's head.

FIG. 8 is side view and top plan view showing another example of the probe in FIG. 6 attached to the head of the subject 6. If the head is rather smaller than the probe, the distance between only one pair of incident and detection points on the outer periphery of the gap 4 is shortened so as to reduce the size in only one direction. Further, as the connecting members 3, which are rotatable about the incident and detection points, are fit to the head, the connecting members partially form a diamond mesh structure. The outermost periphery of the probe also has a diamond mesh structure so as to be attached to the head avoiding the ears of the subject 6.

Figure 9:
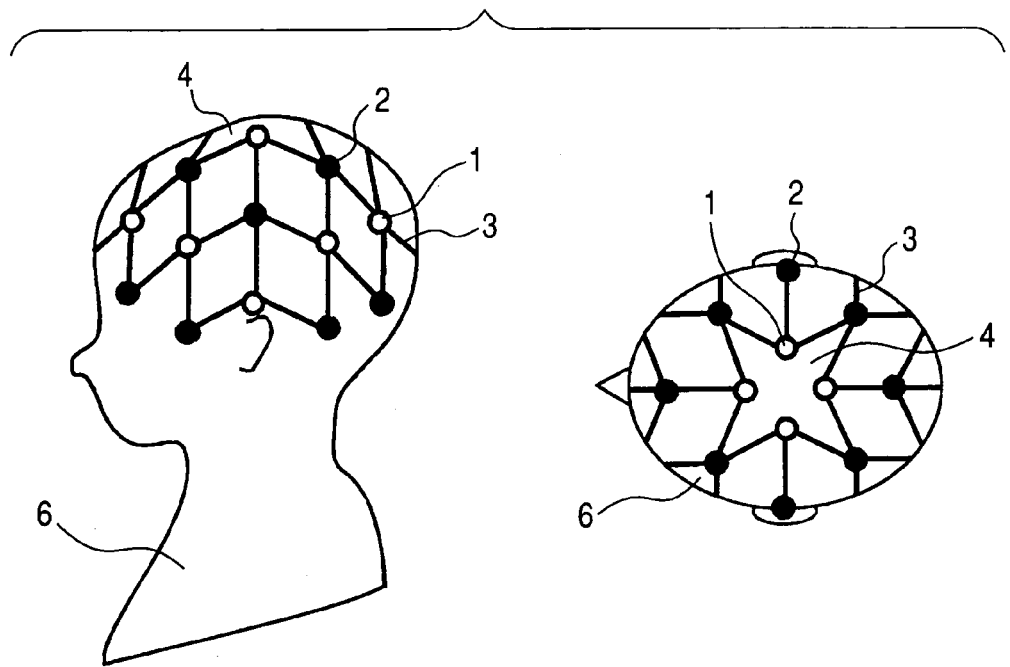
FIG. 9 is side view and top plan view showing another example of the probe in FIG. 6 attached to the subject's head.

FIG. 9 is side view and top plan view showing another example of the probe in FIG. 6 attached to the subject 6. If the head is smaller than the probe, the distances between the two pairs of the incident and detection points on the outer periphery of the gap 4 are shortened, so as to reduce the size in the two directions. Further, as the connecting members 3, which are rotatable about the incident and detection points, are fit to the head, the connecting members partially form a diamond mesh structure. The outermost periphery of the probe also has a diamond mesh structure so as to be attached to the head avoiding the ears of the subject 6. If the corner angle of the diamond mesh is sharp and part of incident and detection points cover the face, the part of incident and detection points may be removed. Otherwise, part of incident and detection points may be provided as removable.

In the above probe, as a mechanism to maintain the angle of the outer periphery of the gap 4 and maintain approximately constant distances between the incident points 1 or the detection points 2, part of the connecting members 3 may be fixed. Further, the slidability of part of the connecting members 3 is degraded so as to maintain once-fixed status.

Figure 10:
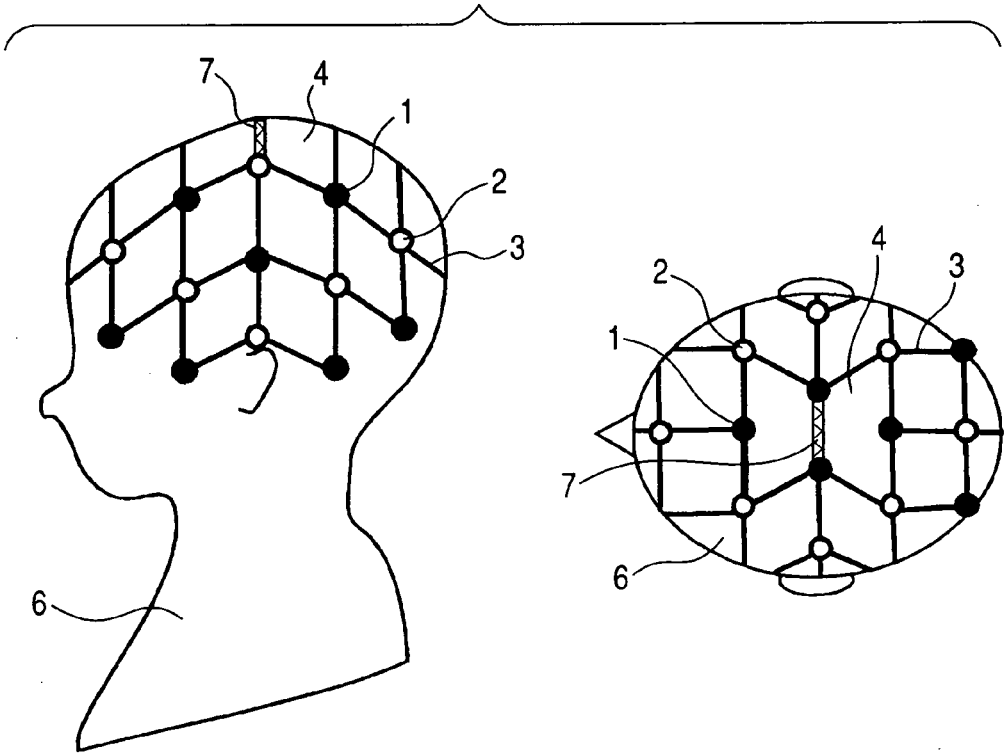
FIG. 10 is side view and top plan view showing an example of a method of maintaining the angle of the outer periphery of a gap and holding a constant shortened distance between incident points or detection points in the probe in FIG. 6.

FIG. 10 is side view and top plan view showing an example of the method of maintaining the angle of the outer periphery of the gap 4 and holding a constant shortened distance between incident points 1 or the detection points 2 in the probe in FIG. 6.

A pair of opposite detection points on the outer periphery of the gap 4 are connected with a string member (or a belt member) 7, and the length of the string member 7 is changed, thereby the distance in one direction can be adjusted.

Figure 11:
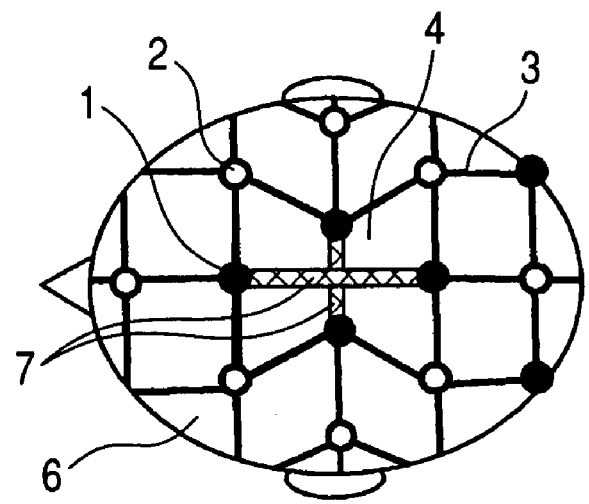
FIG. 11 is a plan view showing another example of the method of maintaining the angle of the outer periphery of the gap and holding a constant shortened distance between the incident points or the detection points in the probe in FIG. 6.

FIG. 11 is a plan view showing another example of the method of maintaining the angle of the outer periphery of the gap 4 and holding a constant shortened distance between the incident points 1 or the detection points 2 in the probe in FIG. 6.

Two pairs of opposite detection points on the outer periphery of the gap 4 are connected with two string members 7, and the lengths of the string members 7 are changed, thereby the distances in two directions can be adjusted.

Figure 12:
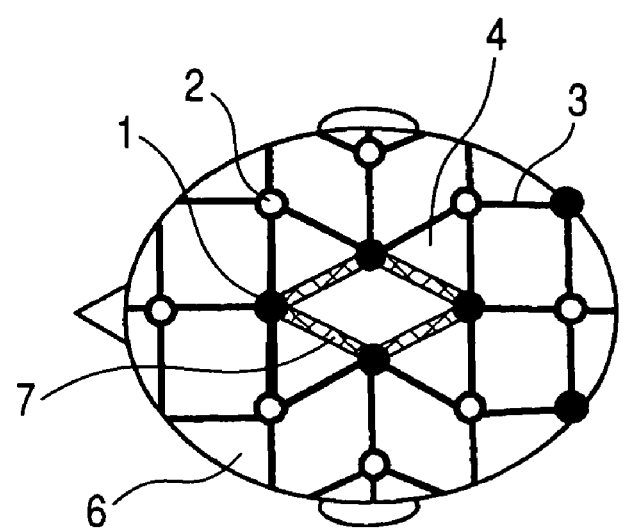
FIG. 12 is a plan view showing another example of the method of maintaining the angle of the outer periphery of the gap and holding a constant shortened distance between the incident points or the detection points in the probe in FIG. 6.

FIG. 12 is a plan view showing another example of the method of maintaining the angle of the outer periphery of the gap 4 and holding a constant shortened distance between the incident points 1 or the detection points 2 in the probe in FIG. 6.

Two pairs of opposite detection points on the outer periphery of the gap 4 are connected with one string member 7, and the area of the gap 4 is reduced by adjusting the length of the string members 7 as if the opening of a bag is tightened, thereby the distances in two directions can be adjusted.

Figure 13:
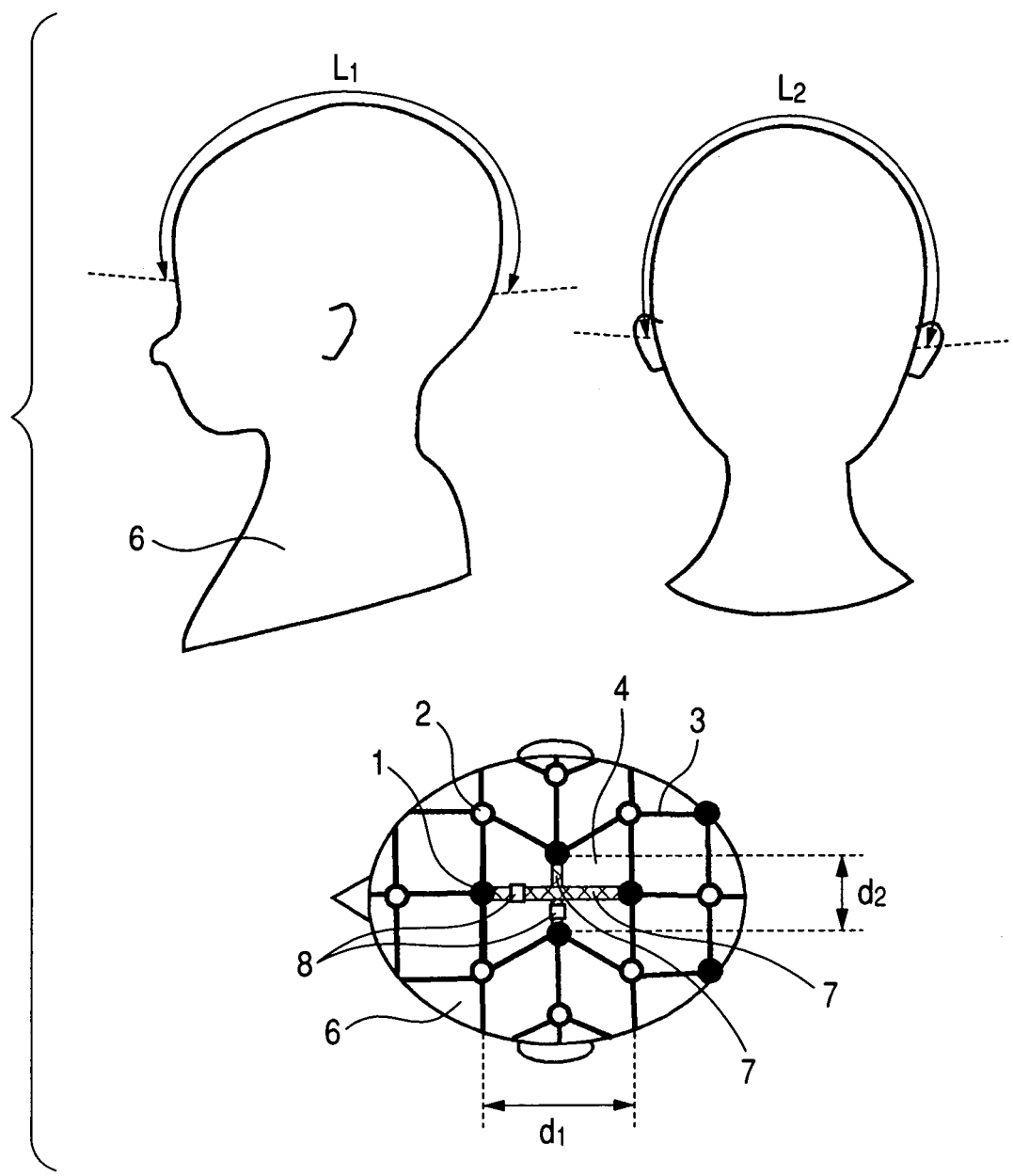
FIG. 13 is side view, front view and top plan view showing a method of fixing the distance between the incident points and the detection points using strings in the probe in FIG. 6.

FIG. 13 is side view, front view and top plan view showing a method of fixing the distance between the incident points and the detection points using strings in the probe in FIG. 6. A length adjustment member 8 is attached to the string member 7 so as to adjust the length of the string member 7 as the fixing member in correspondence with the size of the head. The length adjustment by the length adjustment member 8 may be performed when the probe has been attached to the subject's head, or may be performed before the probe is attached to the head. As adjustment prior to attachment, the following method, for example, is applicable.

Assuming that (i) the distance connecting both ends of an area to be covered with the probe, e.g., projecting portions of the forehead and the occipital region in the front-back direction is L1, (ii) the distance connecting the bases of the ears in the left-right direction is L2, (iii) the distance between the incident point 1 and the detection point 2 is r, (iv) the arrangement of the probe is as shown in FIG. 6, the length d1 of the string in the front-back direction and the length d2 of the string in the left-right direction are estimated as follows.

$$d1 = L1 - 4r \quad (1)$$

$$d2 = L2 - 4r \quad (2)$$

It may be arranged such that the probe where the length of the string 7 has been previously set to the length d1, the length d2 or an approximate value to this, is attached to the head. Note that in the arrangements in FIGS. 1 to 4, the lengths are estimated as follows.

$$d1 = L1 - 6r \quad (3)$$

$$d2 = L2 - 6r \quad (4)$$

Figure 14:
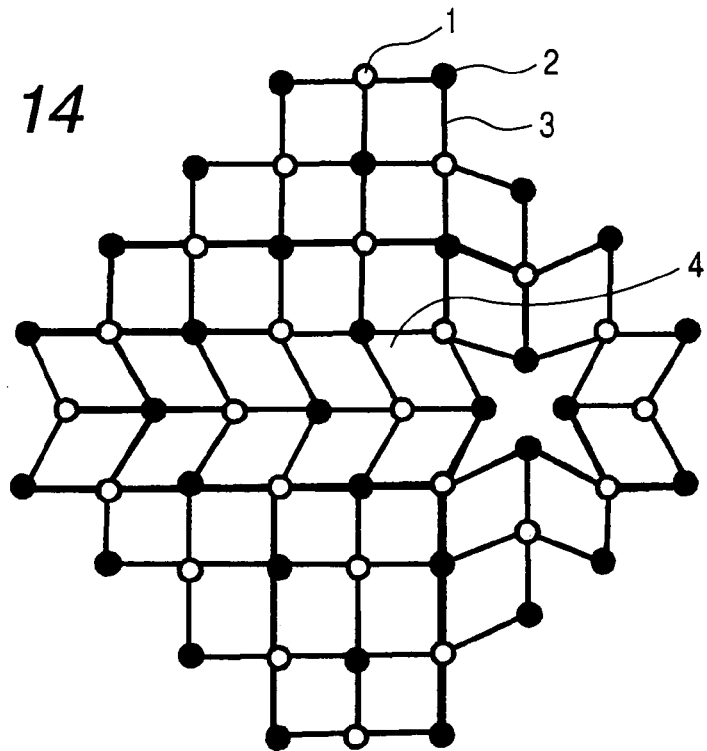
FIG. 14 is an expansion plan view showing another arrangement of the probe for biomeasurement by use of light according to the present invention.

FIG. 14 is an expansion plan view showing another arrangement of the probe for biomeasurement by use of light according to the present invention. The gap 4 is shifted from the center of the probe arrangement corresponding to the head top portion. The gap 4 can be provided in, e.g., the frontal region, the occipital region, the right temporal region or the left temporal region, in corresponding to a portion to be measured, and a brain function image including the head top portion can be obtained.

Figure 15:
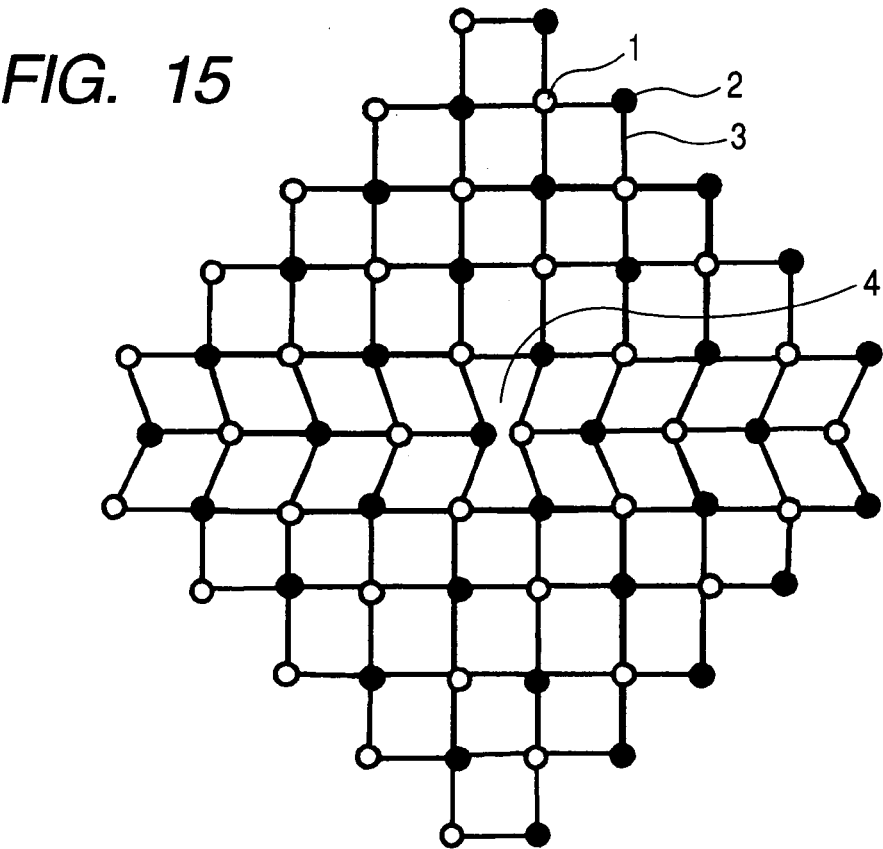
FIG. 15 is an expansion plan view showing another arrangement of the probe for biomeasurement by use of light according to the present invention.

FIG. 15 is an expansion plan view showing another arrangement of the probe for biomeasurement by use of light according to the present invention. In the above probe arrangement, four connecting members 3 are removed so as to form a comparatively wide gap 4, however, if the difference in head size is small, it may be arranged such that only one connecting member 3 is removed so as to form a small gap 4, as shown in FIG. 15.

Figure 16:
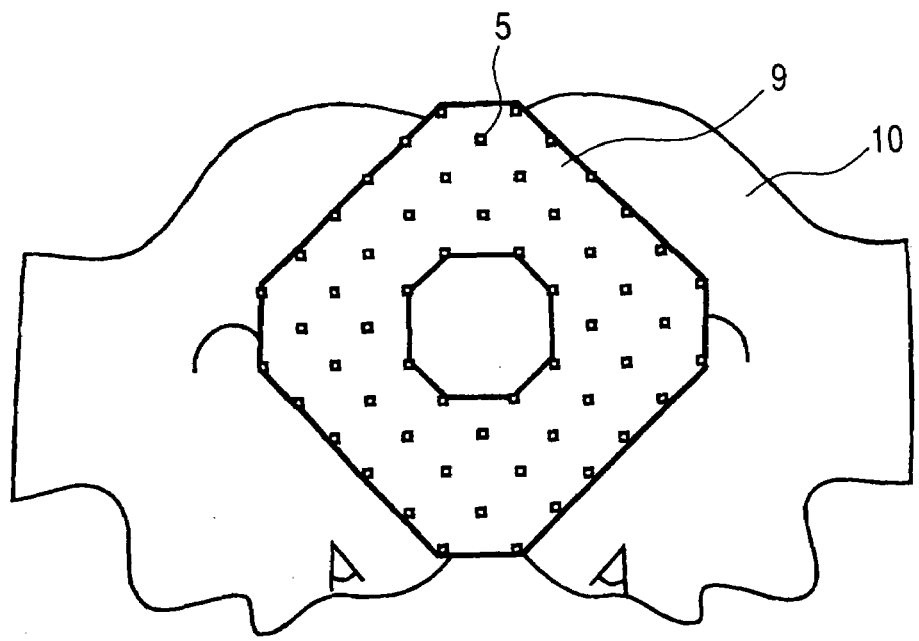
FIG. 16 illustrates an example of a method of displaying a brain function image obtained by the probe for biomeasurement by use of light according to the present invention.

FIG. 16 illustrates an example of a method of displaying a brain function image obtained by the probe for biomeasurement by use of light according to the present invention.

As the connecting members 3 in the probe rotate about the incident points 1 or the detection points 2, the arrangement of the incident points 1 and the detection points 2 has a diamond mesh structure, and the probe is attached so as to fit along the head. Accordingly, an actual brain function image is a curved surface. However, it is difficult to display such curved surface on a two-dimensional monitor or paper sheet. Accordingly, the arrangement of the incident points 1 and the detection points 2, actually deformed as diamond mesh structure so as to fit along the head, is corrected to a square lattice configuration on screen display. The positions of the sampling points 5 are also corrected in accordance with the correction of the positions of the incident and detection points.

A similar correction is performed on a head image (computer graphic, illustration, photograph or the like) superpose-displayed with the brain function image to a distorted image, such that the correspondence between the brain activity and the portion of activity in the head can be easily understood. In FIG. 16, a brain function image is superposed on a plan head image 10 where temporal regions are emphasized. For example, this arrangement is available for display of auditory sense or speech function which locally exists in the temporal regions.

Figure 17:
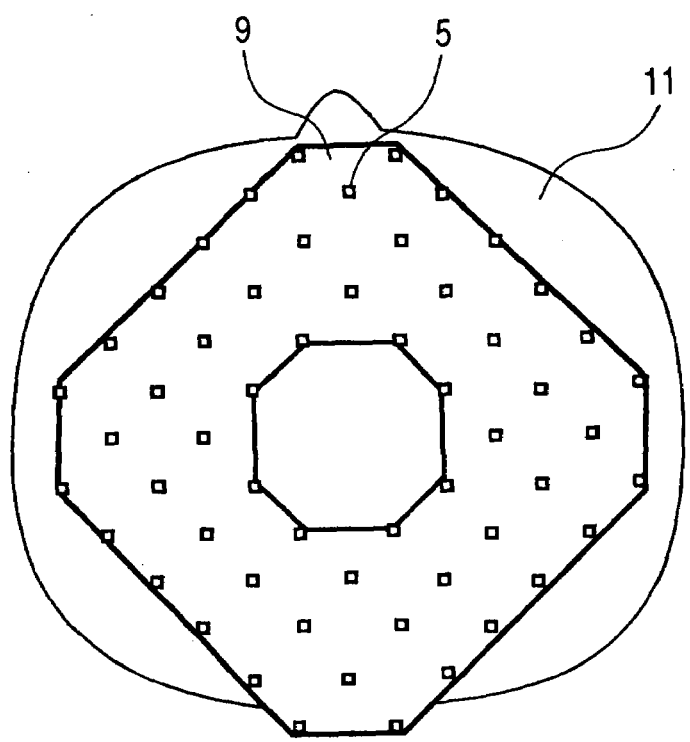
FIG. 17 illustrates another example of the method of displaying a brain function image obtained by the probe for biomeasurement by use of light according to the present invention.

FIG. 17 illustrates another example of the method of displaying a brain function image obtained by the probe for biomeasurement by use of light according to the present invention. A brain function image is superposed on a plan head image 11 which is distorted by correction, such that the brain activity in the entire head can be easily understood.

Figure 18:
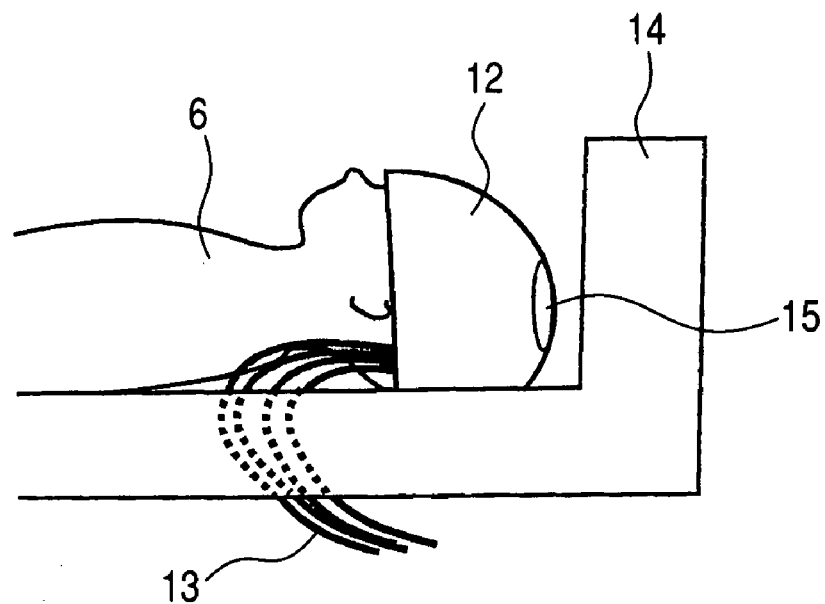
FIG. 18 is a side view showing an example of a method of fixing the probe for biomeasurement by use of light according to the present invention when the probe is attached to the subject.

FIG. 18 is a side view showing an example of a method of fixing the probe for biomeasurement by use of light according to the present invention when the probe is attached to the subject.

A stretch probe cap (or helmet) 12 is laid over the probe, thereby the entire probe is fixed and is prevented from dropping. The probe cap 12 and the probe may be fixed with each other for prevention of slipping, or may not be fixed with each other. Otherwise, the probe and the probe cap 12 may be integrated so as to be attached at once. Further, a hole 15 may be provided in approximately the same position of the gap 4.

Further, upon measurement of a newborn infant or a patient, it may be arranged such that the patient, with the probe cap 12 on the head, is subjected to measurement while the subject is lying down. In this case, the probe cap 12 may be fixed to a bed 14 so as to prevent the head from moving, otherwise, may not be fixed such that the head can move. In the case of newborn infant who cannot move his/her head by himself/herself, the probe may be easily attached when the probe cap 12 is fixed to the bed 14. Optical fibers 13, connected to the incident points 1 or the detection points 2, and extending outward from a lower part of the probe cap 12, may be inserted through the bed 14 so as not to be buried under the subject 6. In FIG. 18, as the optical fibers 13 are pulled out from the lower part of the probe cap 12, the hole 15 in the position corresponding to the gap 4 at the cap top may be omitted.

Figure 19:
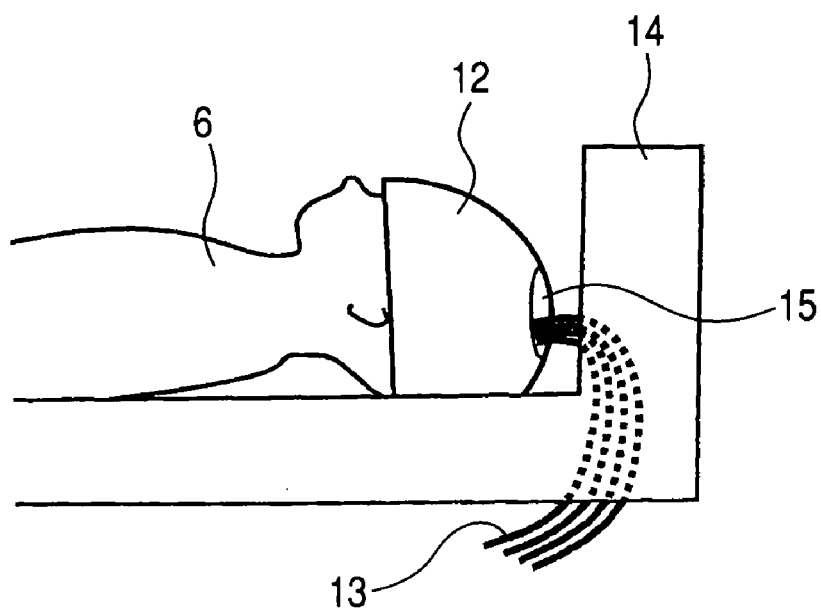
FIG. 19 is a side view showing another example of the method of fixing the probe for biomeasurement by use of light according to the present invention when the probe is attached to the subject.

FIG. 19 is a side view showing another example of the method of fixing the probe for biomeasurement by use of light according to the present invention when the probe is attached to the subject.

As in the case of FIG. 18, the subject wearing the probe cap 12 is lying down, however, the optical fibers 13 connecting to the incident points 1 or the detection points 2 are pulled out from the hole 15 at the head top portion. Further, the optical fibers 13 may be inserted through the bed 14. Further, to avoid the influence of body motion on the optical fiber 13 which influences signal transmission status, the optical fibers 13 may be bunched and fixed to the bed with an elastic member.

Figure 20:
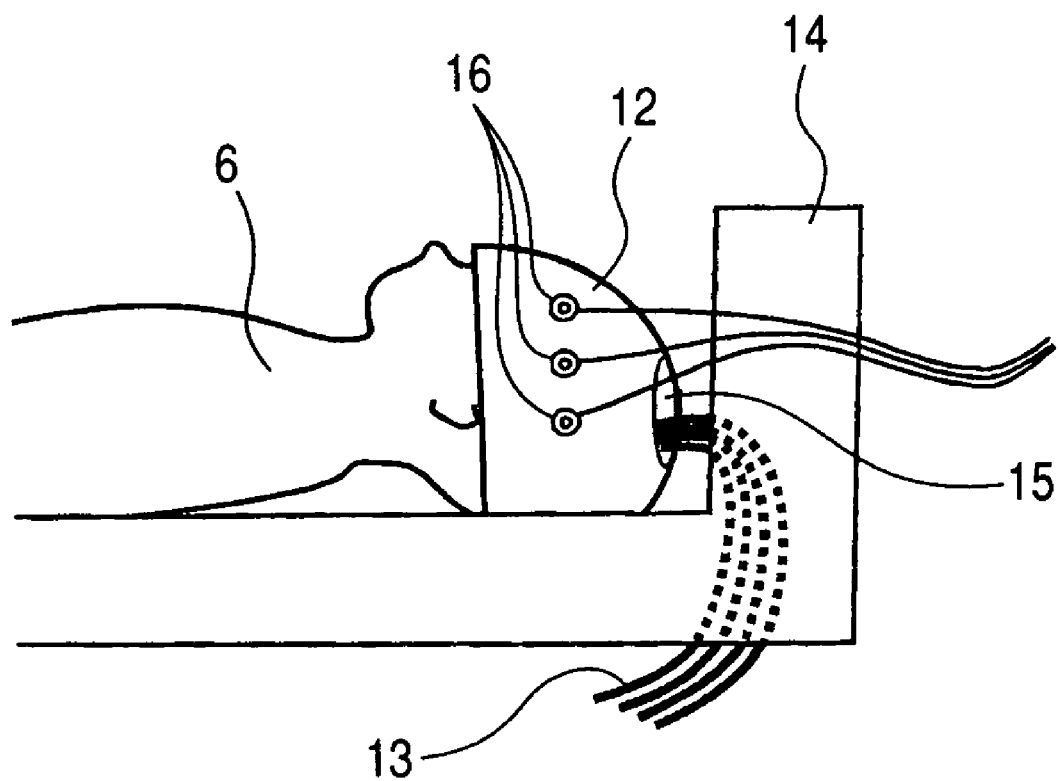
FIG. 20 is a side view showing another example of the method of fixing the probe for biomeasurement by use of light according to the present invention when the probe is attached to the subject.

FIG. 20 is a side view showing another example of the method of fixing the probe for biomeasurement by use of light according to the present invention when the probe is attached to the subject.

A brain wave electrode 16 may be attached to the probe cap 12 such that a brain wave can also be measured. The brain wave measurement may be used for measuring the same brain function as that in the brain function measurement by light, or may be used for monitoring another function or status. For example, wakefulness may be monitored. Accordingly, the number of samplings may be the same as or smaller than the number of light samplings. Further, the number of samplings may be larger than the number of light samplings.

As described above, the present invention can realize a probe for biomeasurement by use of light capable of measuring the entire head. The probe is capable of performing measurement in relatively the same positions even when the size of a subject's head changes, by adjusting positions of incident points and detection points without changing the distance between the incident point and the detection point, in accordance with the size of the subject's head.

What is claimed is:

1. A probe for biomeasurement by use of light comprising:
plural emission optical fibers adapted to emit light to a subject;
plural detection optical fibers adapted to detect light, emitted from the emission optical fibers and propagated inside the subject;
plural fixing units that respectively fix the emission optical fibers and the detection optical fibers; and
connecting members that each have approximately a same length and respectively connect the plural fixing units;
wherein distances between adjacent fixing units connected with the connecting members are approximately the same;
wherein the connecting member is rotatable about the fixing unit; and
wherein a gap having a variable area, in which the fixing units and the connecting members are omitted, is surrounded by the connecting members having approximately the same length, and is provided in a part of the entire area constructed with the plural fixing units and the plural connecting members.

2. The probe for biomeasurement by use of light according to claim 1, wherein the distance between the fixing units, provided around the gap, and not adjacent to each other, is variable.

3. The probe for biomeasurement by use of light according to claim 1, further comprising a fixing member that fixes the distance between the fixing units, provided around the gap, and not adjacent to each other.

4. The probe for biomeasurement by use of light according to claim 3, wherein the fixing member has a length adjustment mechanism.

5. The probe for biomeasurement by use of light according to claim 1, wherein, to fix the distance between the fixing units, provided around the gap and not adjacent to each other, the connecting member between the fixing units provided around the gap fixes rotation about the fixing unit.

6. The probe for biomeasurement by use of light according to claim 1, wherein the fixing unit and the connecting member are removable, so as to increase/decrease the number of the fixing units.

7. The optical bioinstrumentation according to claim 1, wherein each fixing unit of the plural fixing units fixes one of an emission optical fiber and a detection optical fiber.

8. An optical bioinstrumentation comprising:
a probe having plural emission optical fibers that emit light to a subject and plural detection optical fibers that detect transmission light, emitted from the emission optical fibers and propagated inside the subject, adapted to be attached to the subject; and
a computation unit that calculates the density of metabolites in the subject from the transmission light detected by the probe;
wherein the probe has plural fixing units that respectively fix the emission optical fibers and the detection optical fibers, and connecting members that each have approximately a same length and respectively connect the plural fixing units;
wherein distances between adjacent fixing units connected with the connecting units are approximately the same;
wherein the connecting member is rotatable about the fixing unit; and
wherein a gap having a variable area, in which the fixing units and the connecting members are omitted, is surrounded by the connecting members having approximately the same length, and is provided in a part of the entire area constructed with the plural fixing units and the plural connecting members.

9. The optical bioinstrumentation according to claim 8, wherein the distance between the fixing units, provided around the gap in the probe, and not adjacent to each other, is variable.

10. The optical bioinstrumentation according to claim 8, further comprising a fixing member that fixes the distance between the fixing units, provided around the gap in the probe, and not adjacent to each other.

11. The optical bioinstrumentation according to claim 10, wherein the fixing member has a length adjustment mechanism.

12. The optical bioinstrumentation according to claim 8, wherein, to fix the distance between the fixing units, provided around the gap in the probe and not adjacent to each other, the connecting member between the fixing units provided around the gap fixes rotation about the fixing unit.

13. The optical bioinstrumentation according to claim 8, wherein the fixing unit and the connecting member in the probe are removable, so as to increase/decrease the number of the fixing units.

14. The optical bioinstrumentation according to claim 8, wherein the computation unit calculates the density of metabolites in the subject in an approximately middle position between the emission optical fiber and the detection optical fiber as a measuring point, based on a signal detected by the probe.

15. The optical bioinstrumentaion according to claim 8, wherein each fixing unit of the plural fixing units fixes one of an emission optical fiber and a detection optical fiber.

* * * * *